United States Patent [19]

Hansen et al.

[11] Patent Number: 5,371,080
[45] Date of Patent: Dec. 6, 1994

[54] IMIDAZOQUINAZOLINE COMPOUNDS AND THEIR USE

[75] Inventors: Holger C. Hansen, Vaerløse; Marit Kristiansen, Soborg, both of Denmark

[73] Assignee: Novo Nordisk A/S, Bagsvaerd

[21] Appl. No.: 991,077

[22] Filed: Dec. 15, 1992

Related U.S. Application Data

[63] Continuation-in-part of Ser. No. 712,324, Jun. 7, 1991, abandoned.

[30] Foreign Application Priority Data

Jun. 22, 1990 [DK] Denmark .................. 1518/90
Dec. 20, 1991 [DK] Denmark .................. 2042/91

[51] Int. Cl.$^5$ .................. A61K 31/535; A61K 31/54; C07D 487/04
[52] U.S. Cl. .................. 514/228.5; 514/233.2; 514/267; 544/60; 544/115; 544/230; 544/250
[58] Field of Search .................. 544/250, 60, 115, 230; 514/267, 233.2, 228.5

[56] References Cited

U.S. PATENT DOCUMENTS

| | | | |
|---|---|---|---|
| 4,031,079 | 6/1977 | Mohrbacher et al. | 260/239.3 |
| 4,359,420 | 11/1982 | Gerecke et al. | 260/239.3 |
| 4,771,051 | 9/1988 | Wätjen et al. | 514/267 |
| 4,774,245 | 9/1988 | Wätjen et al. | 514/250 |
| 4,873,244 | 10/1989 | Wätjen et al. | 514/250 |

FOREIGN PATENT DOCUMENTS

| | | |
|---|---|---|
| 0225013 | 6/1987 | European Pat. Off. |
| 0226282 | 6/1987 | European Pat. Off. |
| 0283162 | 9/1988 | European Pat. Off. |
| 0320136 | 6/1989 | European Pat. Off. |
| 0344943 | 12/1989 | European Pat. Off. |
| 0347094 | 12/1989 | European Pat. Off. |

OTHER PUBLICATIONS

Hansen, *Chemical Abstracts*, vol. 116, No. 174168 (1992) (Abstract for WO 9200298, Jan. 9, 1992).

*Primary Examiner*—Emily Bernhardt
*Attorney, Agent, or Firm*—Steve T. Zelson; Elias J. Lambiris

[57] ABSTRACT

Imidazoquinazoline compounds having the formula

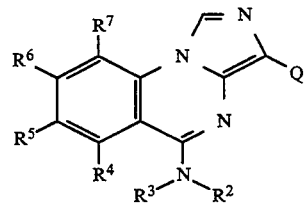

wherein Q is

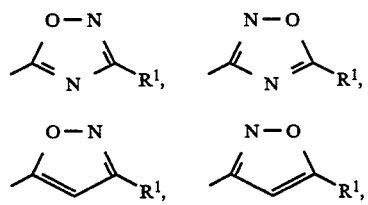

—COOR$^8$ or —CN; wherein R$^1$ is H, alkyl, unsubstituted or substituted cycloalkyl, alkoxy, alkoxyalkyl or CF$_3$; R$^8$ is alkyl; R$^2$ and R$^3$ independently are H, alkyl optionally substituted, hydroxyalkyl, alkoxy, alkoxyalkyl, alkoxycarbonylalkyl, formylalkyl, or an acetal thereof, or R$^2$ and R$^3$ together with the N-atom form a 4-6 membered monocyclic amino group in which ring system one or more of the carbon atoms may be exchanged with N, O or S, sulphinyl, sulphonyl or carbonyl or an acetal thereof, each of these ring systems optionally being substituted; R$^4$, R$^5$, R$^6$ and R$^7$ independently are H, OH, halogen, CF$_3$, NO$_2$, NH$_2$, CN, alkyl, alkenyl, alkynyl, alkoxy, alkoxyalkyl or alkoxycarbonyl.

The compounds are useful in psychopharmaceutical preparations as anticonvulsants, anxiolytics, hypnotics, antipsychotics, antiemetics, in improving the cognitive function of the brain of mammals, or as benzodiazepine antagonists.

36 Claims, No Drawings

IMIDAZOQUINAZOLINE COMPOUNDS AND THEIR USE

This is a continuation-in-part of copending Ser. No. 07/712,324, filed June 7, 1991, now abandoned.

The present invention relates to therapeutically active imidazoquinazoline compounds, a method of preparing the same, pharmaceutical compositions comprising the compounds, and to methods of treating therewith. The novel compounds are useful in psychopharmaceutical applications, e.g. in the treatment of central nervous system ailments, for example as anticonvulsants, anxiolytics, hypnotics, antipsychotics, antiemetics, in improving the cognitive function of the brain of mammals, or as benzodiazepine antagonists.

It is well known (Squires, R. F. and Braestrup, C. in Nature (London) 266 (1977) 732–734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinazoline compounds have strong affinity for the benzodiazepine receptors which make them useful in psychopharmaceutical preparations.

Accordingly, it is an object of the invention to provide such novel imidazoquinazoline compounds.

The compounds of the invention have the general formula I

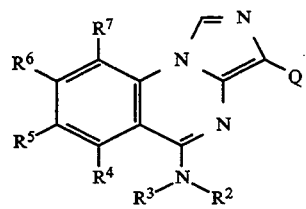

(I)

or pharmaceutically acceptable acid addition salts or hydrates thereof, wherein Q is

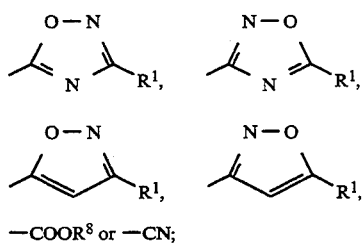

—COOR$^8$ or —CN;

wherein R$^1$ is hydrogen, straight or branched C$_{1-6}$-alkyl, unsubstituted or C$_{1-6}$-alkyl substituted C$_{3-7}$-cycloalkyl, C$_{1-6}$-alkoxy, C$_{1-6}$-alkoxy-C$_{1-6}$-alkyl or trifluoromethyl; R$^8$ is straight or branched C$_{1-6}$-alkyl;

R$^2$ and R$^3$ independently are hydrogen, C$_{1-6}$-alkyl, optionally substituted with C$_{3-7}$-cycloalkyl, di-C$_{1-6}$-alkylamino, phenyl or a piperidinyl group optionally substituted with C$_{1-6}$-alkyl, or R$^2$ and R$^3$ independently are C$_{3-7}$-cycloalkyl, C$_{1-6}$-hydroxyalkyl, C$_{1-6}$-alkoxy, C$_{1-6}$-alkoxy-C$_{1-6}$-alkyl, C$_{1-6}$-alkoxycarbonyl-C$_{1-6}$-alkyl, formyl-C$_{1-6}$-alkyl or a cyclic or non-cyclic acetal thereof, or R$^2$ and R$^3$ together with the nitrogen atom form a 4–6 membered cyclic amino group in which ring system one or more of the carbon atoms may be exchanged with nitrogen, oxygen, sulphur, sulphinyl, sulphonyl or carbonyl or a hydrate, an acyclic or a cyclic acetal thereof, each of these ring systems optionally being substituted with one or more of C$_{1-6}$-alkyl, C$_{1-6}$-alkoxymethyl, hydroxy, C$_{1-6}$-hydroxyalkyl or phenyl;

R$^4$, R$^5$, R$^6$ and R$^7$ independently are hydrogen, hydroxy, Cl, Br, F, I, trifluoromethyl, nitro, amino, cyano, straight or branched C$_{1-6}$-alkyl, C$_{2-6}$-alkenyl, C$_{2-6}$-alkynyl, C$_{1-6}$-alkoxy, C$_{1-6}$-alkoxy-C$_{1-6}$-alkyl or C$_{1-6}$-alkoxycarbonyl;

The invention also relates to methods of preparing the above-mentioned compounds. These methods comprise:

a) reacting a compound of formula II

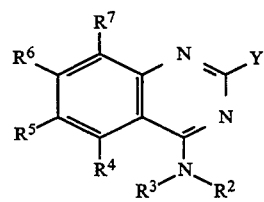

(II)

wherein R$^2$, R$^3$, R$^4$, R$^5$, R$^6$ and R$^7$ are as defined above and wherein Y is a leaving group, with a compound having the formula III

CN—CH$_2$—Q   (III)

wherein Q is as defined above, to form a compound of the general formula I, or b) reacting a reactive derivative of a compound having the general formula IV

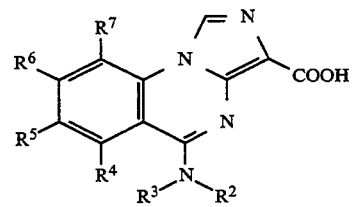

(IV)

wherein R$^2$, R$^3$, R$^4$, R$^5$, R$^6$, and R$^7$ are as defined above with a compound having the general formula V

R$^1$—C(=NOH)NH$_2$   (V)

wherein R$^1$ is as defined above to form a compound of the general formula I wherein Q is

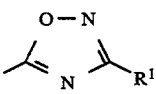

wherein R$^1$ is as defined above, or c) reacting a compound of the general formula VI

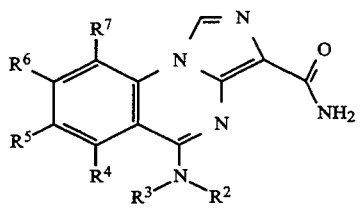

(VI)

wherein $R^2$, $R^3$, $R^4$, $R^5$, $R^6$ and $R^7$ have the meanings set forth above, with a dehydrating agent to form a compound of formula I, wherein $R^2$, $R^3$, $R^4$, $R^5$, $R^6$ and $R^7$ have the meanings set forth above and wherein Q is cyano or d) reacting a compound of formula VII

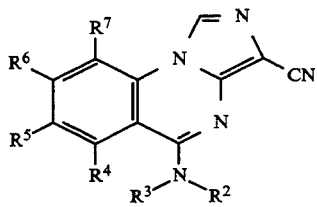

(VII)

wherein $R^2$, $R^3$, $R^4$, $R^5$, $R^6$ and $R^7$ have the meanings set forth above, with $NH_2OH$ to form a compound of formula VIII

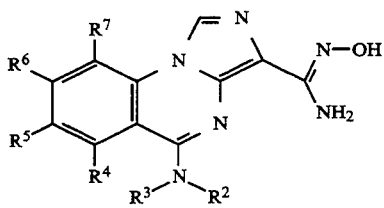

(VIII)

wherein $R^2$, $R^3$, $R^4$, $R^5$, $R^6$ and $R^7$ have the meanings set forth above, and reacting the compound of formula VIII with $R^1$-COOEt or with $(R^1CO)_2O$, wherein $R^1$ is as defined above to form a compound of the general formula I wherein Q is

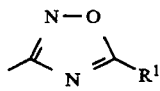

wherein $R^1$ is as defined above, or e) hydrolysis of a compound of the general formula I to form a compound of the general formula IX

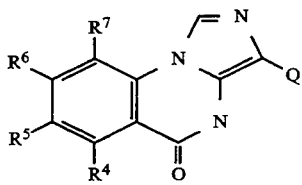

(IX)

wherein Q, $R^4$, $R^5$, $R^6$, and $R^7$ have the meanings set forth above, and reacting the compound of formula IX with $POCl_3$ to form a compound of formula X

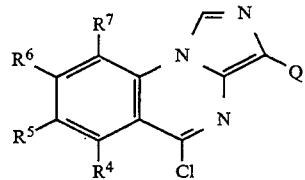

(X)

which is reacted with a compound of formula XI $NHR^2R^3$ (XI)

wherein $R^2$ and $R^3$ have the meanings set forth above, to form a compound of the general formula I.

The leaving group, Y, may be any suitable leaving group and, for example, those disclosed in U.S. Pat. Nos. 4,031,079 or 4,359,420, for example, halogen, alkylthio, for example methylthio, aralkylthio, N-nitrosoalkylamino, alkoxy, mercapto, —OPO(O)(OR)$_2$ wherein R is lower-alkyl or —OP(O)(NR'R'')$_2$ wherein R' and R'' each represents lower-alkyl or phenyl, or together with the nitrogen atom to which they are attached represent a heterocyclic radical such as morpholino, pyrrolidino, piperidino, or methypiperazinyl. The reaction is preferably carried out under alkaline conditions, i.e., in the presence of a base, and among bases alkali metal (e.g., potassium or sodium) alkoxides or hydrides are preferred. The reaction is preferably conducted in the presence of an organic solvent which is nonreactive with the reactants and products of reaction under the conditions of reaction, especially an anhydrous solvent and preferably and anhydrous aprotic solvent such as dimethylformamide (DMF), tetrahydrofuran (THF), or the like. The temperature range employed may be any range suitable for the reaction to proceed at a reasonable rate and without undue delay or decomposition and a range from —40° C. to about room temperature is accordingly usually particularly suitable.

The starting materials employed in the syntheses of the compounds of formula I are either known or may be prepared in conventional manner from commercially available materials, e.g. according to Karminski et al., J. Environ. Sci. Health, Part B, 1983 B 18 (4–5) 599.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of $^3H$-flunitrazepam to benzodiazepine receptors in a living brain to be reduced to 50% of the control value.

Such an in vivo test is carried out as described in U.S. Pat. No. 4,774,245.

Test results obtained by testing some compounds of the invention will appear from the following table I.

TABLE I

| Compound | $ED_{50}$ (mg/kg) |
|---|---|
| 1 | 2.9 |
| 3 | 0.44 |
| 20 | 0.29 |
| 24 | 0.5 |
| XIII | 1.5 |
| XIV | 1.9 |
| XIX | 1.6 |

TABLE I-continued

| Compound | ED$_{50}$ (mg/kg) |
| --- | --- |
| IV | 4.1 |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing 0.1-100 mg of active ingredient or, more specified, 1.0-50 mg per tablet, are accordingly suitable representative unit dosage forms.

The compounds of the invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or the like can be used when a sweetened vehicle can be employed. Generally, as to broader ranges, the compounds of the invention are dispensed in unit dosage form comprising 0.05-100 mg in a pharmaceutically acceptable carrier per unit dosage.

A typical tablet which may be prepared by conventional tabletting techniques contains:

| | |
| --- | --- |
| Active compound | 1.0 mg |
| Lactosum | 67.8 mg Ph. Eur. |
| Avicel ® | 31.4 mg |

-continued

| | |
| --- | --- |
| Amberlite ® IRP 88 | 1.0 mg |
| Magnesii stearas | 0.25 mg Ph. Eur. |

Due to their high degree of affinity for the benzodiazepine receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, anxiolytic, hypnotic, antipsychotic, and antiemetic activities and activity as to improvement of the cognitive function of the brain of mammals along with a low toxicity, together presenting a most favourable therapeutic index. The compounds of the invention may accordingly be administered to a subject, e.g. a living mammal body, including a human, in need of the same for the treatment, alleviation, amelioration, or elimination of an indication, associated with the central nervous system and the so-called benzodiazepine receptors, which requires such psychopharmaceutical treatment, e.g. especially convulsion, insomnia, anxiety, psychosis, emesis, dementia states and/or as benzodiazepine antagonists, if desired in the form of a pharmaceutically acceptable acid addition salt thereof (such as the hydrobromide, hydrochloride, tartrate or sulphate, in any event prepared in the usual or conventional manner, e.g. evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective psychopharmaceutical central nervous system aliment alleviating amount, e.g. an anticonvulsant, anxiolytic, hypnotic and/or antipsychotic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which may not be construed as limiting:

EXAMPLE 1

3-(3-Cyclopropyl-1,2,4-oxadiazol-5-yl)-5-morpholino-6-trifluoromethyl-imidazo[1,5-a]quinazoline (Compound 1)

To a stirred solution of 2-chloro-4-morpholino-5-trifluoromethyl-quinazoline (600 mg, 1.9 mmol) and 3-cyclopropyl-5-isocyanomethyl-1,2,4-oxadiazole (440 mg, 2.9 mmol) in dry DMF (15 ml) under nitrogen at 5°-10° C. was added solid potassium t-butoxide (330 mg, 2.9 mmol). The mixture was stirred at 5°-10° C. for 0.5 h and triturated with water (20 ml). The crystals were filtered off and washed with water (10 ml) and ethyl acetate. A final purification was done by stirring the crystals in acetone (10 ml) to give 330 mg of the title compounds, m.p. 197°–199° C.

¹H-nmr (CDCl₃) δ: 8.4 (s, 1H, imidazo-), 8.2–7.9 (m, 3H, benzo-), 4.0–3.2 (m, 8H, morpholino-), 2.2 (m, 1H, CH), 1.3–1.0 (m, 4H, CH₂).

EXAMPLE 2

3-(3-Cyclopropyl-1,2,4-oxadiazol-5-yl)-6-methyl-5-morpholino-imidazo[1,5-a]-quinazoline (Compound 2)

A mixture of 2-chloro-5-methyl-4-morpholino-quinazoline (1.68 g, 6.4 mmol) and 3-cyclopropyl-5-isocyanomethyl-1,2,4-oxadiazole (1.9 g) in 15 ml of dry dimethylformamide was cooled to 0° C. Solid potassium tert-butoxide (1.4 g, 12.5 mmol) was added gradually during 5 min. to the stirred mixture, the temperature being kept below 10° C. The mixture was stirred at ambient temperature for two hors, and then cooled to 0° C. The precipitated crystals were collected by filtration, rinsed on the filter with ethyl acetate and water, and dried to give the title compound as light yellow crystals, m.p. 262°–266° C. Yield 1.29 g.

¹H-nmr (CDCl₃) δ: 8.30 (s, 1H, imidazo-), 7.85–7.35 (m, 3H, benzo-), 4.05–3.8 (m, 4H, N-CH₂), 3.75–3.30 (m, 4H, O-CH₂), 2.88 (s, 3H, CH₃), 2.30–2.12 (m, 1H, CH), 1.3–1.0 (m, 4H, CH₂).

In a similar way the following compounds were prepared:

6-Bromo-3-(3-cyclopropyl-1,2,4-oxadiazol-5-yl)-5-morpholino-imidazo[1,5-a]-quinazoline (Compound 3), m.p. 275°–277° C., from 2-chloro-5-bromo-4-morpholino-quinazoline and 3-cyclopropyl-5-isocyanomethyl-1,2,4-oxadiazole;

tert-Butyl 6-methyl-5-thiomorpholino-imidazo[1,5-a]quinazoline-3-carboxylate (Compound 4), m.p. 164°–166° C., from 2-chloro-5-methyl-4-thiomorpholino-quanazoline and tert-butyl isocyanoacetate;

6-Bromo-3-(3-cyclopropyl-1,2,4-oxadiazol-5-yl)-5-(N-(2,2-dimethoxyethyl)-N-methylamino)-imidazo[1,5-a]quinazoline (Compound 5), m.p. 170°–171° C., from 2-chloro-5-bromo-4-(N-(2,2-dimethoxyethyl)-N-methylamino)quinazoline and 3-cyclopropyl-5-isocyanomethyl-1,2,4-oxadiazole;

3-(5-Cyclopropyl-1,2,4-oxadiazol-3-yl)-6-methyl-5-thiomorpholino-imidazo[1,5-a]quinazoline (Compound 6), m.p. 205°–206° C., from 2-chloro-5-methyl-4-thiomorpholino-quinazoline and 5-cyclopropyl-3-isocyanomethyl-1,2,4-oxadiazole;

6-Bromo-3-(3-cyclopropyl-1,2,4-oxadiazol-5-yl)-5-(N-ethoxycarbonylmethyl-N-methylamino)-imidazo[1,5-a]quinazoline (Compound 7), m.p. 189°–191° C. from 2-chloro-5-bromo-4-(N-ethoxycarbonylmethyl-N-methylamino)quinazoline and 3-cyclopropyl-5-isocyanomethyl-1,2,4-oxadiazole;

7-Chloro-3-(3-cyclopropyl-1,2,4-oxadiazol-5yl)-5-(N,N-bis(2-methoxyethyl)amino)-imidazo[1,5-a]quinazoline (Compound 8), m.p. 212°–215° C., from 2,6-dichloro-4-(N,N-bis(2-methoxyethyl)amino)-quinazoline and 3-cyclopropyl-5-isocyanomethyl-1,2,4-oxadiazole;

7-Chloro-3-(3-cyclopropyl-1,2,4-oxadiazol-5-yl)-5-(N-(1,3-dioxolan-2-yl)methyl-N-methylamino)-imidazo[1,5-a]quinazoline (Compound 9), m.p. 223°–226° C., from 2,6-dichloro-4-(N-(1,3-dioxolan-2-yl)methyl-N-methylamino)quinazoline and 3-cyclopropyl-5-isocyanomethyl-1,2,4-oxadiazole;

3-(3-Cyclopropyl-1,2,4-oxadiazol-5-yl)-7-fluoro-5-morpholino-imidazo[1,5-a]-quinazoline (Compound 10), m.p. 243°–245° C., from 2-chloro-6-fluoro-4-morpholino-quinazoline and 3-cyclopropyl-5-isocyanomethyl-1,2,4-oxadiazole;

Ethyl 7-fluoro-5-morpholino-imidazo[1,5-a]quinazoline-3-carboxylate (Compound 11), m.p. 238°–239° C., from 2-chloro-6-fluoro-4-morpholino-quinazoline and ethyl isocyanoacetate;

Isopropyl 7-chloro-5-(N-(1,3-dioxolan-2-yl)methyl-N-methylamino)imidazo[1,5-a]quinazoline-3-carboxylate (Compound 12), m.p. 135°–137° C., from 2,6-dichloro-4-(N-(1,3-dioxolan-2-yl)-methyl-N-methylamino)quinazoline and isopropyl isocyanoacetate;

9-Chloro-3-(3-cyclopropyl-1,2,4-oxadiazol-5-yl)-5-morpholino-imidazo[1,5-a]-quinazoline (Compound 13), m.p. 121°–124° C., from 2,8-dichloro-4-morpholino-quinazoline and 3-cyclopropyl-5-isocyanomethyl-1,2,4-oxadiazole;

9-Chloro-3-(3-cyclopropyl-1,2,4-oxadiazol-5-yl)-5-(4-methyl-1-piperazinyl)imidazo[1,5-a]quinazoline (Compound 14), m.p. 199°–201° C., from 2,8-dichloro-4-(4-methyl-1-piperazinyl)quinazoline and 3-cyclopropyl-5-isocyanomethyl-1,2,4-oxadiazole;

6,9-Dichloro-3-(3-cyclopropyl-1,2,4-oxadiazol-5-yl)-5-morpholino-imidazo[1,5-a]quinazoline (Compound 15), m.p. 184°–186° C., from 2,5,8-trichloro-4-morpholino-quinazoline and 3-cyclopropyl-5-isocyanomethyl-1,2,4-oxadiazole;

7-Chloro-3-(5-methoxymethyl-1,2,4-oxadiazol-3-yl)-5-(N-ethyl-N-methylamino)imidazo[1,5-a]quinazoline (Compound 16), m.p. 169°–172° C., from 2,6-dichloro-4-(N-methyl-N-ethylamino)quinazoline and 3-isocyanomethyl-5-methoxymethyl-1,2,4-oxadiazole;

3-(3-Cyclopropyl-1,2,4-oxadiazol-5-yl)-5-thiomorpholino-6-trifluoromethylimidazo[1,5-a]quinazoline (Compound 17), m.p. 162°–165° C., from 2-chloro-4-thiomorpholino-5-trifluoromethyl-quinazoline and 3-cyclopropyl-5-isocyanomethyl-1,2,4-oxadiazole;

3-(5-Cyclopropyl-1,2,4-oxadiazol-3-yl)-5-thiomorpholino-6-trifluoromethylimidazo[1,5-a]quinazoline (Compound 18), m.p. 155°–158° C., from 2-chloro-4-thiomorpholino-5-trifluoromethyl-quinazoline and 5-cyclopropyl-3-isocyanomethyl-1,2,4-oxadiazole;

6-Cyano-3-(5-cyclopropyl-1,2,4-oxadiazol-3-yl)-5-morpholino-imidazo[1,5-a]quinazoline (Compound 19), m.p. 184°–187° C., from 2-chloro-5-cyano-4-morpholino-quinazoline and 5-cyclopropyl-3-isocyanomethyl-1,2,4-oxadiazole;

3-(3-Cyclopropyl-1,2,4-oxadiazol-5-yl)-6-fluoro-5-morpholino-imidazo[1,5-a]quinazoline (Compound 20), m.p. 216°–218° C., from 2-chloro-5-fluoro-4-morpholino-quinazoline and 3-cyclopropyl-5-isocyanomethyl-1,2,4-oxadiazole;

3-(5-Cyclopropyl-1,2,4-oxadiazol-3-yl)-6-fluoro-5-morpholino-imidazo[1,5-a]-quinazoline (Compound 21), m.p. 204°–207° C., from 2-chloro-5-fluoro-4-morpholino-quinazoline and 5-cyclopropyl-3-isocyanomethyl-1,2,4-oxadiazole;

3-(3-Cyclopropyl-1,2,4-oxadiazol-5-yl)-6-fluoro-5-(cis-2,6-dimethylmorpholino)-imidazo[1,5-a]quinazoline (Compound 22), m.p. 187°–188° C., from 2-chloro-5-fluoro-4-(cis-2,6-dimethyl-morpholino)-quinazoline and 3-cyclopropyl-5-isocyanomethyl-1,2,4-oxadiazole;

3-(3-Cyclopropyl-1,2,4-oxadiazol-5-yl)-6-fluoro-5-thiomorpholino-imidazo[1,5-a]quinazoline (Compound 23), m.p. 252°–253° C., from 2-chloro-5-fluoro4-thiomorpholino-quinazoline and 3-cyclopropyl-5-isocyanomethyl-1,2,4-oxadiazole;

3-(3-Cyclopropyl-1,2,4-oxadiazol-5-yl)-6-fluoro-5-(4-methyl-1-piperazinyl)imidazo[1,5-a]quinazoline (Compound 24), m.p. 258°-260° C., from 2-chloro-5-fluoro-4-(4-methyl-1-piperazinyl)-quinazoline and 3-cyclopropyl-5-isocyanomethyl-1,2,4-oxadiazole;

3-(5-Cyclopropyl-1,2,4-oxadiazol-3-yl)-5-(trans-2,5-dimethylmorpholino)-6-fluoro-imidazo[1,5-a]quinazoline (Compound 25), m.p. 208°-210° C., from 2-chloro-5-fluoro-4-(2,5-dimethylmorpholino)-quinazoline and 5-cyclopropyl-3-isocyanomethyl-1,2,4-oxadiazole. Compound 25 was separated from compound 26 by column chromatography (eluent: ethyl acetate:acetone (2:1));

3-(5-Cyclopropyl-1,2,4-oxadiazol-3-yl)-5-(cis-2,5-dimethylmorpholino)-6-fluoro-imidazo[1,5-a]quinazoline (Compound 26), m.p. 186°-189° C., from 2-chloro-5-fluoro-4-(2,5-dimethylmorpholino)-quinazoline and 5-cyclopropyl-3-isocyanomethyl-1,2,4-oxadiazole. Compound 26 was separated from compound 25 by column chromatography (eluent: ethyl acetate:acetone (2:1));

3-(3-Cyclopropyl-1,2,4-oxadiazol-5-yl)-8-fluoro-5-morpholino-imidazo[1,5-a]-quinazoline (Compound 27), m.p. 276°-278° C., from 2-chloro-7-fluoro-4-morpholino-quinazoline and 3-cyclopropyl-5-isocyanomethyl-1,2,4-oxadiazole;

3-(3-Cyclopropyl-1,2,4-oxadiazol-5-yl)-5-(3,3-dimethylmorpholino)-7-fluoro-imidazo[1,5-a]quinazoline (Compound 28), m.p. 259° C., from 2-chloro-6-fluoro-4-(3,3-dimethylmorpholino)-quinazoline and 3-cyclopropyl-5-isocyanomethyl-1,2,4-oxadiazole;

3-(3-Cyclopropyl-5-isoxazolyl)-6-fluoro-5-morpholino-imidazo[1,5-a]quinazoline (Compound 29), m.p. 208°-210° C., from 2-chloro-5-fluoro-4-morpholino-quinazoline and 3-cyclopropyl-5-isocyanomethyl-isoxazole;

3-(5-Cyclopropyl-1,2,4-oxadiazol-3-yl)-5-(3,3-dimethylmorpholino)-7-fluoro-imidazo[1,5-a]quinazoline (Compound 30), m.p. 251°-254° C., from 2-chloro-6-fluoro-4-(3,3-dimethylmorpholino)-quinazoline and 5-cyclopropyl-3-isocyanomethyl-1,2,4-oxadiazole;

tert-Butyl 6-fluoro-5-morpholino-imidazo[1,5-a]quinazoline-3-carboxylate (Compound 31), m.p. 191°-193° C., from 2-chloro-5-fluoro-4-morpholino-quinazoline and t-butyl isocyanoacetate;

3-(5-Cyclopropyl-1,2,4-oxadiazol-3-yl)-7-fluoro-5-(4-methyl-1-piperazinyl)imidazo[1,5-a]quinazoline (Compound 32), m.p. 202°-204° C. from 2-chloro-6-fluoro-4-(4-methyl-1-piperazinyl)-quinazoline and 5-cyclopropyl-3-isocyanomethyl-1,2,4-oxadiazole;

3-(3-Cyclopropyl-1,2,4-oxadiazol-5-yl)-5-(N-(1,3-dioxolan-2-yl)methyl-N-methylamino)-6-fluoro-imidazo[1,5-a]quinazoline (Compound 33), m.p. 209°-211° C., from 2-chloro-4-(N-(1,3-dioxolan-2-yl)methyl-N-methylamino)-5-fluoro-quinazoline and 3-cyclopropyl-5-isocyanomethyl-1,2,4-oxadiazole;

3-(5-Cyclopropyl-1,2,4-oxadiazol-3-yl)-5-(3,3-dimethylmorpholino)-6-fluoro-imidazo[1,5-a]quinazoline (Compound 34), m.p. 210°-212° C., from 2-chloro-4-(3,3-dimethylmorpholino)-5-fluoro-quinazoline and 5-cyclopropyl-3-isocyanomethyl-1,2,4-oxadiazole;

3-(5-Cyclopropyl-1,2,4-oxadiazol-3-yl)-5-(cis-2,6-dimethyl-1-piperidinyl)-6-fluoro-imidazo[1,5-a]quinazoline (Compound 35), m.p. 163°-164° C., from 2-chloro-4-(cis-2,6-dimethyl-1-piperidinyl)-5-fluoro-quinazoline and 5-cyclopropyl-3-isocyanomethyl-1,2,4-oxadiazole;

3-(5-Cyclopropyl-1,2,4-oxadiazol-3-yl)-7-fluoro-5-thiomorpholino-imidazo[1,5-a]quinazoline (Compound 36), m.p. 233°-235° C., from 2-chloro-6-fluoro-4-thiomorpholino-quinazoline and 5-cyclopropyl-3-isocyanomethyl-1,2,4-oxadiazole;

3-(3-Cyclopropyl-1,2,4-oxadiazol-5-yl)-5-(4-methyl-1-piperazinyl)-6-trifluoromethyl-imidazo[1,5-a]quinazoline, hydrochloride (Compound 37), m.p. decomp. at 300° C., from 2-chloro-4-(4-methyl-1-piperazinyl)-5-trifluoromethyl-quinazoline and 3-cyclopropyl-5-isocyanomethyl-1,2,4-oxadiazole. The hydrochloride was formed by dissolving the base in methylene chloride and adding hydrogen chloride.

Ethyl 6-fluoro-5-morpholino-imidazo[1,5-a]quinazoline-3-carboxylate (Compound 38), m.p. 196°-198° C., from 2-chloro-5-fluoro-4-morpholino-quinazoline and ethyl isocyanoacetate;

3-(5-Cyclopropyl-1,2,4-oxadiazol-3-yl)-5-(4-methyl-1-piperazinyl)-6-trifluoromethyl-imidazo[1,5-a]quinazoline, hydrochloride (Compound 39), m.p. decomp. at 200° C., from 2-chloro-4-(4-methyl-1-piperazinyl)-5-trifluoromethyl-quinazoline and 5-cyclopropyl-3-isocyanomethyl-1,2,4-oxadiazole. The hydrochloride was formed by dissolving the base in methylene chloride and adding hydrogen chloride.

3-(3-Cyclopropyl-1,2,4-oxadiazol-5-yl)-5-(trans-2,5-dimethylmorpholino)-6-fluoro-imidazo[1,5-a]quinazoline (Compound 40), m.p. 211°-214° C., from 2-chloro-5-fluoro-4-(2,5-dimethylmorpholino)-quinazoline and 3-cyclopropyl-5-isocyanomethyl-1,2,4-oxadiazole. Compound 40 was separated from compound 41 by column chromatography (eluent: methylene chloride:ethyl acetate (1:1));

3-(3-Cyclopropyl-1,2,4-oxadiazol-5-yl)-5-(cis-2,5-dimethylmorpholino)-6-fluoro-imidazo[1,5-a]quinazoline (Compound 41), m.p. 169°-171° C., from 2-chloro-5-fluoro-4-(2,5-dimethylmorpholino)-quinazoline and 3-cyclopropyl-5-isocyanomethyl-1,2,4-oxadiazole. Compound 41 was separated from compound 40 by column chromatography (eluent: methylene chloride:ethyl acetate (1:1));

3-(5-Cyclopropyl-1,2,4-oxadiazol-3-yl)-5-(N-(1,3-dioxolan-2-yl)methyl-N-methylamino)-6-fluoro-imidazo[1,5-a]quinazoline (Compound 42), m.p. 184°-186° C., from 2-chloro-4-(N-(1,3-dioxolan-2-yl)methyl-N-methylamino)-5-fluoro-quinazoline and 5-cyclopropyl-3-isocyanomethyl-1,2,4-oxadiazole;

3-(3-Cyclopropyl-1,2,4-oxadiazol-5-yl)-5-(cis-2,6-dimethyl-1-piperidinyl)-6-fluoro-imidazo[1,5-a]quinazoline (Compound 43), m.p. 132°-134° C., from 2-chloro-4-(cis-2,6-dimethyl-1-piperidinyl)-5-fluoro-quinazoline and 3-cyclopropyl-5-isocyanomethyl-1,2,4-oxadiazole;

3-(3-Cyclopropyl-1,2,4-oxadiazol-5-yl)-5-(3,3-dimethylmorpholino)-6-fluoroimidazo[1,5-a]quinazoline (Compound 44), m.p. 244°-246° C., from 2-chloro-4-(3,3-dimethylmorpholino)-5-fluoro-quinazoline and 3-cyclopropyl-5-isocyanomethyl-1,2,4-oxadiazole;

3-(3-Cyclopropyl-1,2,4-oxadiazol-5-yl)-5-(N-(2-dimethylaminoethyl)-N-ethylamino)-7-fluoro-imidazo[1,5-a]quinazoline (Compound 45), m.p. 170°-172° C., from 2-chloro-6-fluoro-4-(N-(2-dimethylaminoethyl)-N-ethylamino)-quinazoline and 3-cyclopropyl-5-isocyanomethyl-1,2,4-oxadiazole.

EXAMPLE 3

6-Chloro-3-(3-cyclopropyl-1,2,4-oxadiazol-5-yl)-4,5-dihydro-5-oxo-imidazo[1,5-a]quinazoline 6-Chloro-3-(3-cyclopropyl-1,2,4-oxadiazol-5-yl)-5-morpholino-imidazo[1,5-a]quinazoline (1.45 g) in 25 ml of 6M aqueous hydrochloric acid was stirred at 100° C. for 45 min. Then the mixture was cooled to 0° C. and the precipitated crystals were filtered off, rinsed on the filter with 25 ml of water, then with 5×1 ml of ethyl acetate, and finally with 10 ml of diethyl ether. The beige crystals were dried, yielding 0.85 g of the title compound, m.p. 270°–272° C. (decomp.).

In a similar way the following compounds were prepared:

3-(5-Cyclopropyl-1,2,4-oxadiazol-3-yl)-6-fluoro-4,5-dihydro-5-oxo-imidazo[1,5-a]quinazoline, m.p. 260°–264° C. (decomp.), by hydrolysis of 3-(5-cyclopropyl-1,2,4-oxadiazol-3-yl)-6-fluoro-5-(3,5-dimethylmorpholino)-imidazo[1,5-a]quinazoline;

3-(5-Cyclopropyl-1,2,4-oxadiazol-3-yl)-7-fluoro-4,5-dihydro-5-oxo-imidazo[1,5-a]quinazoline, m.p. 254°–255° C., by hydrolysis of 3-(5-cyclopropyl-1,2,4-oxadiazol-3-yl)-7-fluoro-5-(3,3-dimethylmorpholino)-imidazo[1,5-a]quinazoline.

EXAMPLE 4

5,6-Dichloro-3-(3-cyclopropyl-1,2,4-oxadiazol-5-yl)-imidazo[1,5-a]quinazoline

A stirred mixture of 6-chloro-3-(3-cyclopropyl-1,2,4-oxadiazol-5-yl)-4,5-dihydro-5-oxo-imidazo[1,5-a]quinazoline (1.0 g), tripropylamine (0.5 ml) and phosphorus oxychloride (5 ml) was heated at 140°–150° C. After 1 hour, more POCl$_3$ (5 ml) and tripropylamine (0.5 ml) was added, and heating was continued for 1½ hours. Then the warm mixture was poured into 200 ml of ice water with vigorous stirring. After 15 min. 100 ml of dichloromethane was added. Undissolved material was collected by filtration, rinsed with diethyl ether and dried to give the title compound as tan crystals, m.p. 238°–240° C. Yield 0.47 g.

In a similar way the following compounds were prepared:

5-Chloro-3-(5-cyclopropyl-1,2,4-oxadiazol-3-yl)-6-fluoro-imidazo[1,5-a]-quinazoline, from 3-(5-cyclopropyl-1,2,4-oxadiazol-3-yl)-6-fluoro-4,5-dihydro-5-oxo-imidazo[1,5-a]quinazoline;

5-Chloro-3-(5-cyclopropyl-1,2,4-oxadiazol-3-yl)-7-fluoro-imidazo[1,5-a]-quinazoline, m.p. 249°–251° C., from 3-(5-cyclopropyl-1,2,4-oxadiazol-3-yl)-7-fluoro-4,5-dihydro-5-oxo-imidazo[1,5-a]quinazoline.

EXAMPLE 5

(R)-6-chloro-3-(3-cyclopropyl-1,2,4-oxadiazol-5-yl)-5-(2-hydroxymethyl-1-pyrrolidinyl)-imidazo[1,5-a]quinazoline (Compound 46)

A mixture of (R)-2-hydroxymethylpyrrolidine (70 mg) and triethylamine (90 mg) dissolved in dry DMF (1 ml) was added dropwise to a stirred suspension of 5,6-dichloro-3-(3-cyclopropyl-1,2,4-oxadiazol-5-yl)-imidazo[1,5-a]-quinazoline (0.20 g) in dry DMF (5 ml) at 0° C. After 20 min. the reaction mixture was filtered. The filtrate was diluted with 15 ml of water and stirred at 0° C. for 10 min. The crystals which had formed were filtered off, rinsed with water, and dried to give the title compound as yellow crystals, m.p. 220°–221° C. Yield 0.15 g.

In the same way the following compounds were prepared:

6-Chloro-3-(3-cyclopropyl-1,2,4-oxadiazol-5-yl)-5-thiomorpholino-imidazo[1,5-a]quinazoline (Compound 47), m.p. 240°–241° C., from 5,6-dichloro-3-(3-cyclopropyl-1,2,4-oxadiazol-5-yl)-imidazo[1,5-a]quinazoline and thiomorpholine;

6-Chloro-3-(3-cyclopropyl-1,2,4-oxadiazol-5-yl)-5-(cis-2,6-dimethylmorpholino)-imidazo[1,5-a]quinazoline (Compound 48), m.p. 236°–238° C., from 5,6-dichloro-3-(3-cyclopropyl-1,2,4-oxadiazol-5-yl)-imidazo[1,5-a]quinazoline and cis-2,6-dimethylmorpholine;

(S)-6-Chloro-3-(3-cyclopropyl-1,2,4-oxadiazol-5-yl)-5-(2-methoxymethyl-1-pyrrolidinyl)-imidazo[1,5-a]quinazoline (Compound 49), m.p. 266°–269° C., from 5,6-dichloro-3-(3-cyclopropyl-1,2,4-oxadiazol-5-yl)-imidazo[1,5-a]-quinazoline and (S)-2-methoxymethyl-pyrrolidine;

(S)-6-Chloro-3-(3-cyclopropyl-1,2,4-oxadiazol-5-yl)-5-(2-hydroxymethyl-1-pyrrolidinyl)-imidazo[1,5-a]quinazoline (Compound 50), m.p. 230°–232° C., from 5,6-dichloro-3-(3-cyclopropyl-1,2,4-oxadiazol-5-yl)-imidazo[1,5-a]-quinazoline and (S)-2-hydroxymethyl-pyrrolidine;

6-Chloro-3-(3-cyclopropyl-1,2,4-oxadiazol-5-yl)-5-(3-hydroxy-1-piperidinyl)-imidazo[1,5-a]quinazoline (Compound 51), m.p. 258°–261° C., from 5,6-dichloro-3-(3-cyclopropyl-1,2,4-oxadiazol-5-yl)-imidazo[1,5-a]quinazoline and 3-hydroxypiperidine;

6-Chloro-3-(3-cyclopropyl-1,2,4-oxadiazol-5-yl)-5-(4-phenyl-1-piperazinyl)-imidazo[1,5-a]quinazoline (Compound 52), m.p. 255°–257° C., from 5,6-dichloro-3-(3-cyclopropyl-1,2,4-oxadiazol-5-yl)-imidazo[1,5-a]quinazoline and 1-phenylpiperazine;

6-Chloro-3-(3-cyclopropyl-1,2,4-oxadiazol-5-yl)-5-(4-methyl-1-piperazinyl)-imidazo[1,5-a]quinazoline (Compound 53), m.p. 273°–275° C., from 5,6-dichloro-3-(3-cyclopropyl-1,2,4-oxadiazol-5-yl)-imidazo[1,5-a]quinazoline and 1-methylpiperazine;

6-Chloro-3-(3-cyclopropyl-1,2,4-oxadiazol-5-yl)-5-(4-(2-hydroxyethyl)-1-piperazinyl)-imidazo[1,5-a]quinazoline (Compound 54), m.p. 252°–254° C., from 5,6-dichloro-3-(3-cyclopropyl-1,2,4-oxadiazol-5-yl)-imidazo[1,5-a]quinazoline and 1-(2-hydroxyethyl)piperazine;

5-Amino-6-chloro-3-(3-cyclopropyl-1,2,4-oxadiazol-5-yl)-imidazo[1,5-a]quinazoline (Compound 55), m.p. 343° C., from 5,6-dichloro-3-(3-cyclopropyl1,2,4-oxadiazol-5-yl)-imidazo[1,5-a]quinazoline and aqueous ammonia;

6-Chloro-3-(3-cyclopropyl-1,2,4-oxadiazol-5-yl)-5-(4-propyl-1-piperazinyl)imidazo[1,5-a]quinazoline (Compound 56), m.p. 186°–188° C., from 5,6-dichloro-3-(3-cyclopropyl-1,2,4-oxadiazol-5-yl)-imidazo[1,5-a]quinazoline and 1-propylpiperazine;

3-(5-Cyclopropyl-1,2,4-oxadiazol-3-yl)-6-fluoro-5-morpholino-imidazo[1,5-a]-quinazoline (Compound 21), m.p. 204°–206° C., from 5-chloro-3-(5-cyclopropyl-1,2,4-oxadiazol-3-yl)-6-fluoro-imidazo[1,5-a]quinazoline and morpholine;

5-(N-Cyclopropylmethyl-N-methylamino)-3-(5-cyclopropyl-1,2,4-oxadiazol-3-yl)-7-fluoro-imidazo[1,5-a]quinazoline (Compound 57), m.p. 176°–177° C., from 5-chloro-3-(5-cyclopropyl-1,2,4-oxadiazol-3-yl)-7-fluoro-imidazo[1,5-a]quinazoline and (N-methylaminomethyl)cyclopropane;

3-(5-Cyclopropyl-1,2,4-oxadiazol-3-yl)-7-fluoro-5-(3-thiazolidinyl)imidazo[1,5-a]quinazoline (Compound 58), m.p. 240°–242° C., from 5-chloro-3-(5-cyclopropyl-1,2,4-oxadiazol-3-yl)-7-fluoro-imidazo[1,5-a]quinazoline and thiazolidine;

3-(5-Cyclopropyl-1,2,4-oxadiazol-3-yl)-7-fluoro-5-morpholino-imidazo[1,5-a]-quinazoline (Compound 59), m.p. 213°–214° C., from 7-fluoro-3-(5-cyclopropyl-1,2,4-oxadiazol-3-yl)-5-chloro-imidazo[1,5-a]quinazoline and morpholine;

3-(5-Cyclopropyl-1,2,4-oxadiazol-3-yl)-5-(1,3-dioxolane-2-spiro-4'-piperidino)-7-fluoro-imidazo[1,5-a]quinazoline (Compound 60), m.p. 245°–246° C., from 5-chloro-3-(5-cyclopropyl-1,2,4-oxadiazol-3-yl)-7-fluoro-imidazo[1,5-a]quinazoline and 1,3-dioxolane-2-spiro-4'-piperidine;

3-(5-Cyclopropyl-1,2,4-oxadiazol-3-yl)-5-(N-(2-dimethylaminoethyl)-N-methylamino)-7-fluoro-imidazo[1,5-a]quinazoline (Compound 61), m.p. 148°–150° C., from 5-chloro-3-(5-cyclopropyl-1,2,4-oxadiazol-3-yl)-7-fluoro-imidazo[1,5-a]-quinazoline and N,N,N'-trimethylethylenediamine; 3-(5-Cyclopropyl-1,2,4-oxadiazol-3-yl)-6-fluoro-5-(4-methyl-1-piperazinyl)-imidazo[1,5-a]quinazoline (Compound 62), m.p. 274°–276° C., from 5-chloro-3-(5-cyclopropyl-1,2,4-oxadiazol-3-yl)-6-fluoro-imidazo[1,5-a]quinazoline and 1-methylpiperazine;

3-(5-Cyclopropyl-1,2,4-oxadiazol-3-yl)-6-fluoro-5-(4-(2-hydroxyethyl)-1-piperazinyl)-imidazo[1,5-a]quinazoline (Compound 63), m.p. 228°–230° C., from 5-chloro-3-(5-cyclopropyl-1,2,4-oxadiazol-3-yl)-6-fluoro-imidazo[1,5-a]quinazoline and 1-(2-hydroxyethyl)piperazine;

3-(5-Cyclopropyl-1,2,4-oxadiazol-3-yl)-7-fluoro-5-(N-(2-hydroxyethyl)-N-methylamino)-imidazo[1,5-a]quinazoline (Compound 64), m.p. 161°–163° C., from 5-chloro-3-(5-cyclopropyl-1,2,4-oxadiazol-3-yl)-7-fluoro-imidazo[1,5-a]quinazoline and 2-(N-methylamino)ethanol;

3-(5-Cyclopropyl-1,2,4-oxadiazol-3-yl)-7-fluoro-5-(4-oxopiperidino)-imidazo[1,5-a]quinazoline (Compound 65), m.p. 234°–236° C. (dec.), from 5-chloro-3-(5-cyclopropyl-1,2,4-oxadiazol-3-yl)-7-fluoro-imidazo[1,5-a]quinazoline and 4-piperidone;

3-(5-Cyclopropyl-1,2,4-oxadiazol-3-yl)-7-fluoro-5-(N-methyl-N-(1-methyl-4-piperidinyl)amino)-imidazo[1,5-a]quinazoline (Compound 66), m.p. 204°–207° C., from 5-chloro-3-(5-cyclopropyl-1,2,4-oxadiazol-3-yl)-7-fluoro-imidazo[1,5-a]quinazoline and 1-methyl-4-(methylamino)piperidine.

EXAMPLE 6

5-Morpholino-imidazo[1,5-a]quinazoline-3-carboxamide

A stirred mixture of ethyl 5-morpholino-imidazo[1,5-a]quinazoline-3-carboxylate (2.0 g) and acetamide (1.2 g) in 20 ml of dry dimethylformamide was heated to 80° C. 30% sodium methoxide in methanol (1 ml) was added and the mixture was stirred at 100° C. for 2 hours, cooled to room temperature and diluted with isopropanol (20 ml). Crystals were filtered off, washed with isopropanol (15 ml), water (20 ml) and diethyl ether (10 ml), and dried to give the title compound as yellow crystals, m.p. >300° C. Yield 1.3 g.

EXAMPLE 7

3-Cyano-5-morpholino-imidazo[1,5-a]quinazoline (Compound 67)

Bromine (0.15 ml) was added dropwise to a solution of triphenylphosphine (0.8 g) in 15 ml of methylene chloride at 5° C. 5-morpholino-imidazo[1,5-a]quinazoline-3carboxamide (0.5 g) and triethylamine (0.83 ml) were added to the solution. The resulting reaction mixture was stirred at room temperature for 3 hours and evaporated in vacuo. Ethyl acetate (10 ml) was added to the residue and crude crystals of the title compound were isolated by filtration. The dried crystals were dissolved in acetone (30 ml) and an excess of hydrogen chloride in diethyl ether was added separating the hydrochloride of the title compound as beige crystals. M.p. 225°–228° C. Yield 0.3 g.

In the same way the following compound was prepared:

3-Cyano-6-methoxy-5-morpholino-imidazo[1,5-a]quinazoline (Compound 68), m.p. 283°–284° C., from 6-methoxy-5-morpholino-imidazo[1,5-a]quinazoline-3-carboxamide.

EXAMPLE 8

5-Morpholino-imidazo[1,5-a]quinazoline-3-carboxamide oxime

A mixture of sodium hydroxide (0.06 g), hydroxylamine hydrochloride (0.10 g) and methanol (3 ml) was stirred for 1 hour at room temperature. The hydroxylamine was isolated as a methanol solution by filtration and washing of the filter cake with methanol (7 ml). This hydroxylamine solution was added to a suspension of 3-cyano-5-morpholino-imidazo[1,5-a]quinazoline (0.16 g) in 5 ml of methanol. The reaction mixture was refluxed for 4 hours, cooled to room temperature and filtered. The crystals were washed with methanol and dried to give the title compound as yellow crystals, m.p. 212°–213° C. Yield 0.17 g.

EXAMPLE 9

5-Morpholino-3-(5-trifluoromethyl-1,2,4-oxadiazol-3-yl)-imidazo[1,5-a]quinazoline (Compound 69)

Trifluoroacetic anhydride (0.15 ml) was added dropwise to a suspension of 5-morpholino-imidazo[1,5-a]quinazoline-3-carboxamide oxime in 4 ml of dry tetrahydrofuran. After stirring for 3 hours at room temperature the reaction mixture was evaporated in vacuo. The residue was dissolved in a mixture of water and ethyl acetate. The organic phase was washed with water, dried over anhydrous magnesium sulphate, and evaporated to dryness. The crystals were rinsed by stirring with isopropanol (3 ml) to give yellow crystals of the title compound, m.p. 182°–186° C. Yield 0.06 g.

EXAMPLE 10

3-(5-Cyclopropyl-1,2,4-oxadiazol-3-yl)-6-methoxy-5-morpholino-imidazo[1,5-a]quinazoline (Compound 70)

A mixture of 6-methoxy-5-morpholino-imidazo[1,5-a]quinazoline-3-carboxamide oxime (0.9 g), ethyl cyclopropylcarboxylate (1.7 g), molecular sieves (3 g), and 80% sodium hydride (0.1 g) in 20 ml of dry DMF was heated for 1½ hours at 120° C. The mixture was cooled to room temperature, diluted with acetic acid (0.5 ml) and methylene chloride (20 ml) and filtered. The filtered mixture was evaporated and the residue was purified by column chromatography (HPLC) (eluent: methylene chloride:acetone (2:1)) to give yellow crystals of the title compound, m.p. 227°–228° C. Yield 0.38 g.

In the same manner the following compound was prepared:

3-(5-(1-Methylcyclopropyl)-1,2,4-oxadiazol-3-yl)-5-morpholino-imidazo[1,5-a]quinazoline (Compound 71), m.p. 232°–236° C., from 5-morpholino-imidazo[1,5- a]quinazoline-3-carboxamide oxime and ethyl 1-methyl-cyclopropyl carboxylate.

EXAMPLE 11

3-(3-Cyclopropyl-1,2,4-oxadiazol-5-yl)-5-(1-oxo-thiomorpholino)-imidazo[1,5-a]quinazoline (Compound 72) and 3-(3-Cyclopropyl-1,2,4-oxadiazol-5-yl)-5-(1,1-dioxo-thiomorpholino)-imidazo[1,5-a]quinazoline (Compound 73)

A solution of 3-(3-cyclopropyl-1,2,4-oxadiazol-5-yl)-5-thiomorpholino-imidazo[1,5-a]quinazoline (0.5 g) and 30% aqueous hydrogen peroxide (0.2 ml) in 15 ml of acetic acid was refluxed for 40 minutes. After cooling to room temperature the crude crystals of 3-(3-cyclopropyl-1,2,4-oxadiazol-5-yl)-5-(1,1-dioxo-thiomorpholino)-imidazo[1,5-a]quinazoline were isolated by filtration. Recrystallization from DMF gave the analytically pure compound. M.p. 328°–335° C. Yield 64 mg.

The filtered acetic acid was evaporated in vacuo. The residue was stirred with water (10 ml) and filtered to give crude crystals of 3-(3-cyclopropyl-1,2,4-oxadiazol-5-yl)-5-(1-oxo-thiomorpholino)-imidazo[1,5-a]quinazoline. Recrystallization from DMF gave the analytically pure compound. M.p. 293°–294° C. Yield 0.2 g.

EXAMPLE 12

7-Fluoro-3-(3-isopropyl-1,2,4-oxadiazol-5-yl)-5-morpholino-imidazo[1,5-a]quinazoline (Compound 74)

A mixture of ethyl 7-fluoro-5-morpholino-imidazo[1,5-a]quinazoline-3-carboxylate (1.6 g), 2-methyl-1-propanecarboxamide oxime (2.4 g), crushed 4 Å molecular sieves (3.5 g), and sodium hydride (0.14 g, 80% in mineral oil) in 20 ml of dry DMF was stirred at ambient temperature. After 1 hour an additional amount of the carboxamide oxime (2.4 g) and sodium hydride suspension (0.14 g) was added, and the mixture was stirred for one more hour. Glacial acetic acid (2 ml) and dichloromethane (50 ml) were added, and after the precipitated product had dissolved the sieves were removed by filtration through celite. The filtrate was evaporated and the residue was triturated with 100 ml of water. The undissolved material was collected by filtration, dried and treated with 25 ml of acetone. Yellow crystals precipitated and were filtered off and dried. Yield 0.47 g, m.p. 262°–264° C.

EXAMPLE 13

Ethyl 5-morpholino-imidazo[1,5-a]quinazoline-3-carboxylate (Compound XII)

A solution of potassium t-butoxide (2.1 g, 19 mmol) in dry DMF (15 ml) was added during 15 min. at 0°–5° C. to a stirred solution of 2-chloro-4-morpholino-quinazoline (3.0 g, 12 mmol) and ethyl isocyanoacetate (2.1 g, 19 mmol) in dry DMF (40 ml). The mixture was stirred at room temperature for 2 hours. Then glacial acetic acid (2 ml) was added and the solvent was evaporated in vacuo. The residue was triturated with a mixture of water (50 ml) and ethyl acetate (10 ml) giving the title compound as a pale yellow precipitate. The product was collected by filtration and rinsed with water and ethyl acetate and dried. Yield 3.6 g (91%), m.p. approx. 165° C., resolidifies to give crystals melting at 195.5°–196.5° C.

In a similar manner the following compounds were prepared:

3-(5-Cyclopropyl-1,2,4-oxadiazol-3-yl)-5-dimethylamino-imidazo[1,5-]quinazoline (Compound XIII), m.p. 175°–176° C., from 2-chloro-4-dimethylamino-quinazoline and 5-cyclopropyl-3-isocyanomethyl-1,2,4-oxadiazole;

3-(5-Cyclopropyl-1,2,4-oxadiazol-3-yl)-5-morpholino-imidazo[1,5-a]quinazoline (Compound XIV), m.p. 203°–205° C., from 2-chloro-4-morpholino-quinazoline and 5-cyclopropyl-3-isocyanomethyl-1,2,4-oxadiazole;

3-(5-Cyclopropyl-1,2,4-oxadiazol-3-yl)-5-(N-ethyl-N-methylamino)-imidazo[1,5-a]quinazoline (Compound XV), m.p. 161°–162° C., from 2-chloro-4-(N-ethyl-N-methylamino)-quinazoline and 5-cyclopropyl-3-isocyanomethyl-1,2,4-oxadiazole;

Ethyl 6-chloro-5-morpholino-imidazo[1,5-a]quinazoline-3-carboxylate (Compound XVI), m.p. 189°–191° C., from 2,5-dichloro-4-morpholino-quinazoline and ethyl isocyanoacetate;

3-(5-Cyclopropyl-1,2,4-oxadiazol-3-yl)-5-thiomorpholino-imidazo[1,5-a]quinazoline (Compound XVII), m.p. 193°–196° C., from 2-chloro-4-thiomorpholino-quinazoline and 5-cyclopropyl-3-isocyanomethyl-1,2,4-oxadiazole;

3-(3-Cyclopropyl-1,2,4-oxadiazol-5-yl)-5-thiomorpholino-imidazo[1,5-a]quinazoline (Compound XVIII), m.p. 228°–233° C., from 2-chloro-4-thiomorpholino-quinazoline and 3-cyclopropyl-5-isocyanomethyl-1,2,4-oxadiazole.

EXAMPLE 14

3-(3-Cyclopropyl-1,2,4-oxadiazol-5-yl)-5-morpholino-imidazo[1,5-a]quinazoline (Compound XIX)

A mixture of ethyl 5-morpholino-imidazo[1,5-a]quinazoline-3-carboxylate (2.5 g, 7.7 mmol), cyclopropanecarboxamide oxime (3.8 g), crushed 4 Å molecular sieves (7.5 g), and sodium hydride (0.3 g, 60% in mineral oil, 7.7 mmol) in 50 ml of dry DMF was stirred at room temperature for 1 hour. Glacial acetic acid (2 ml) and dichloromethane (75 ml) were added, and the mixture was filtered through celite. The filtrate was evaporated and the residue was triturated with water (100 ml). Pale yellow crystals precipitated and were collected by filtration and dried to give 2.3 g of the title compound, m.p. 189°–191° C. A pure product was obtained by recrystallization from $CH_2Cl_2$/ethyl acetate; yield 1.9 g (69%), m.p. 197°–198° C.

In the same way the following compound was prepared:

6-Chloro-3-(3-cyclopropyl-1,2,4-oxadiazol-5-yl)-5-morpholino-imidazo[1,5-a]quinazoline (Compound XX), m.p. 245°–246° C., from ethyl 6-chloro-5-morpholino-imidazo[1,5-a]quinazoline-3-carboxylate and cyclopropanecarboxamide oxime.

We claim:
1. A compound of formula I

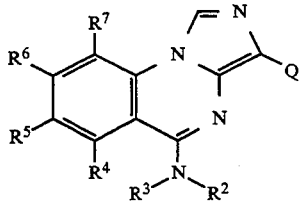

wherein Q is

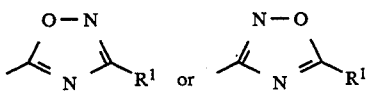

wherein R¹ is H, $C_{1-6}$-alkyl or $C_{3-7}$-cycloalkyl;

R² and R³ independently are H, $C_{1-6}$-alkoxy, $C_{3-7}$-cycloalkyl or $C_{1-6}$-alkyl or NR²R³ is morpholino or thiomorpholino;

R⁴, R⁵, R⁶ and R⁷ are H; or a pharmaceutically acceptable salt thereof.

2. A compound according to claim 1, wherein Q is

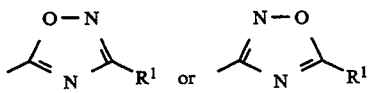

wherein R¹ is cyclopropyl.

3. A compound according to claim 1, wherein R² and R³ independently are hydrogen, methyl or ethyl, or R² and R³ together with the adjacent nitrogen atom form a morpholino or thiomorpholino group.

4. A compound according to claim 1, wherein Q is

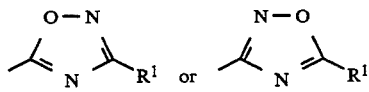

wherein R¹ is cyclopropyl; and

R² and R³ independently are hydrogen, methyl or ethyl, or R² and R³ together with the adjacent nitrogen atom form a morpholino or thiomorpholino group.

5. A compound according to claim 1 which is 3-(5-cyclopropyl-1,2,4-oxadiazol-3-yl)-5-dimethylamino-imidazo[1,5-a]quinazoline or a pharmaceutically acceptable salt thereof.

6. A compound according to claim 1 which is 3-(5-cyclopropyl-1,2,4-oxadiazol-3-yl)-5-morpholino-imidazo[1,5-a]quinazoline or a pharmaceutically acceptable salt thereof.

7. A compound according to claim 1 which is 3-(5-cyclopropyl-1,2,4-oxadiazol-3-yl)-5-thiomorpholino-imidazo[1,5-a]quinazoline or a pharmaceutically acceptable salt thereof.

8. A compound according to claim 1 which is 3-(3-cyclopropyl-1,2,4-oxadiazol-5-yl)-5-morpholino-imidazo[1,5-a]quinazoline or a pharmaceutically acceptable salt thereof.

9. A pharmaceutical composition comprising a compound according to claim 1 together with a pharmaceutically-acceptable carrier or diluent.

10. The pharmaceutical composition according to claim 9 in the form of an oral dosage unit containing 1-100 mg of the active compound.

11. A method for treating a central nervous system ailment associated with benzodiazepine receptors, comprising administering to a subject in need thereof an effective amount of a compound according to claim 1.

12. A method for treating a central nervous system ailment associated with benzodiazepine receptors, comprising administering to a subject in need thereof a pharmaceutical composition according to claim 9.

13. A compound which is ethyl 6-chloro-5-morpholino-imidazo[1,5-a]quinazoline-3-carboxylate or a pharmaceutically acceptable salt thereof.

14. A compound which is 6-chloro-3-(3-cyclopropyl-1,2,4-oxadiazol-5-yl)-5-morpholino-imidazo[1,5-a]quinazoline or a pharmaceutically acceptable salt thereof.

15. A compound of formula I

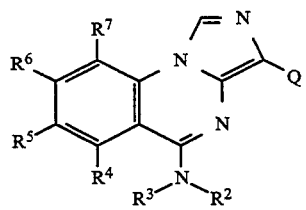

wherein

R² and R³ independently are hydrogen, $C_{1-6}$-alkyl, $C_{1-6}$-alkyl substituted with hydroxy, $C_{1-6}$-alkoxy, —$C_{1-6}$-alkyl-$C_{1-6}$-alkoxy, -$C_{1-6}$-alkyl-carbonyl-$C_{1-6}$-alkoxy, dimethoxyethyl, $C_{1-6}$-alkyl substituted with formyl, $C_{1-6}$-alkyl substituted with 1,3-dioxolan-2-yl; or R² and R³ together with the adjacent nitrogen atom form a morpholino, thiomorpholino, pyrrolidinyl or piperazinyl group wherein said group is optionally substituted with one or more of $C_{1-6}$-alkyl, -methyl-$C_{1-6}$-alkoxy, hydroxy or $C_{1-6}$-alkyl substituted with hydroxy;

R⁴, R⁵, R⁶ and R⁷ independently are hydrogen, hydroxy, Cl, Br, F, I, trifluoromethyl, nitro, amino, cyano, straight or branched $C_{1-6}$-alkyl, $C_{2-6}$-alkenyl, $C_{2-6}$-alkynyl, $C_{1-6}$-alkoxy, —$C_{1-6}$-alkyl-$C_{1-6}$-alkoxy or -carbonyl-$C_{1-6}$-alkoxy; and Q is

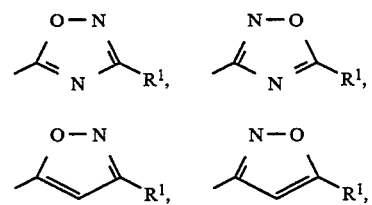

—COOR⁸ or —CN, wherein R¹ is hydrogen, straight or branched $C_{1-6}$-alkyl, $C_{3-7}$-cycloalkyl, $C_{1-6}$-alkoxy, —$C_{1-6}$-alkyl-$C_{1-6}$-alkoxy or trifluoromethyl; and R⁸ is straight or branched $C_{1-6}$-alkyl; or a pharmaceutically acceptable salt or hydrate thereof.

16. A compound according to claim 15, wherein Q is $$\underset{N}{\overset{O-N}{\bigtriangleup}}R^1, \quad \underset{N}{\overset{N-O}{\bigtriangleup}}R^1 \text{ or } -COOR^8$$

wherein $R^1$ is methyl substituted with methoxy, or cyclopropyl; and $R^8$ is ethyl, isopropyl or tert-butyl.

17. A compound according to claim 15, wherein $R^2$ and $R^3$ independently are hydrogen, methyl, ethyl, ethyl substituted with methoxy, dimethoxyethyl, -methyl-carbonyl-ethoxy or -methyl(1,3-dioxolan-2-yl) or $R^2$ and $R^3$ together with the adjacent nitrogen atom form a morpholino, thiomorpholino, pyrrolidinyl or piperazinyl group wherein said group is optionally substituted with one or two of methyl or methyl substituted with hydroxy.

18. A compound according to claim 15, wherein $R^4$, $R^5$, $R^6$ and $R^7$ independently are hydrogen, Cl, Br, F, trifluoromethyl or methyl.

19. A compound according to claim 15, wherein
$R^2$ and $R^3$ independently are hydrogen, methyl, ethyl, ethyl substituted with methoxy, dimethoxyethyl, -methyl-carbonyl-ethoxy or -methyl(1,3-dioxolan-2-yl) or $R^2$ and $R^3$ together with the adjacent nitrogen atom form a morpholino, thiomorpholino, pyrrolidinyl or piperazinyl group wherein said group is optionally substituted with one or more of methyl or methyl substituted with hydroxy;

$R^4$, $R^5$, $R^6$ and $R^7$ independently are hydrogen, Cl, Br, F, trifluoromethyl or methyl; and Q is $$\underset{N}{\overset{O-N}{\bigtriangleup}}R^1, \quad \underset{N}{\overset{N-O}{\bigtriangleup}}R^1 \text{ or } -COOR^8,$$

wherein $R^1$ is methyl substituted with methoxy, or cyclopropyl; and $R^8$ is ethyl, isopropyl or tert-butyl.

20. The compound according to claim 15 which is 3-(3-cyclopropyl-1,2,4-oxadiazol-5-yl)-7-fluoro-5-morpholino-imidazoquinazoline or a pharmaceutically acceptable salt or hydrate thereof.

21. A pharmaceutical composition comprising a compound according to claim 15 together with a pharmaceutically-acceptable carrier or diluent.

22. The pharmaceutical composition according to claim 21 in the form of an oral dosage unit containing 1–100 mg of the active compound.

23. A method for treating a central nervous system ailment associated with benzodiazepine receptors, comprising administering to a subject in need thereof an effective amount of a compound according to claim 15.

24. A method for treating a central nervous system ailment associated with benzodiazepine receptors, comprising administering to a subject in need thereof a pharmaceutical composition according to claim 21.

25. A compound of formula I (structure of formula I with substituents $R^4, R^5, R^6, R^7, R^2, R^3$ and Q)

wherein
$R^2$ and $R^3$ together with the adjacent nitrogen atom form a morpholino, thiomorpholino, pyrrolidinyl or piperazinyl ring wherein said ring is substituted with phenyl; or $R^2$ and $R^3$ together with the adjacent nitrogen atom form a piperidinyl, thiazolidinyl, 1,3-dioxolane-2-spiro-4'-piperidino, oxopiperidino, 1-oxothiomorpholino or 1,1-dioxothiomorpholino group wherein said group is optionally substituted with one or more of $C_{1-6}$-alkyl, methyl-$C_{1-6}$-alkoxy, hydroxy, $C_{1-6}$-alkyl substituted with hydroxy or phenyl;

$R^4$, $R^5$, $R^6$ and $R^7$ independently are hydrogen, hydroxy, Cl, Br, F, I, trifluoromethyl, nitro, amino, cyano, straight or branched $C_{1-6}$-alkyl, $C_{2-6}$-alkenyl, $C_{2-6}$-alkynyl, $C_{1-6}$-alkoxy, —$C_{1-6}$-alkyl-$C_{1-6}$-alkoxy or -carbonyl-$C_{1-6}$-alkoxy; and
Q is $$\underset{N}{\overset{O-N}{\bigtriangleup}}R^1, \quad \underset{N}{\overset{N-O}{\bigtriangleup}}R^1,$$

$$\overset{O-N}{\bigtriangleup}R^1, \quad \overset{N-O}{\bigtriangleup}R^1,$$

—$COOR^8$ or —CN, wherein $R^1$ is hydrogen, straight or branched $C_{1-6}$-alkyl, $C_{3-7}$-cycloalkyl, $C_{1-6}$-alkoxy, —$C_{1-6}$-alkyl-$C_{1-6}$-alkoxy or trifluoromethyl; and $R^8$ is straight or branched $C_{1-6}$-alkyl; or a pharmaceutically acceptable salt or hydrate thereof.

26. A compound according to claim 25, wherein
$R^2$ and $R^3$ together with the adjacent nitrogen atom form a piperazinyl ring substituted with phenyl; or $R^2$ and $R^3$ together with the adjacent nitrogen atom form a piperidinyl, thiazolidinyl, 1,3-dioxolane-2-spiro-4'-piperidino, oxopiperidino, 1-oxothiomorpholino or 1,1-dioxothiomorpholino group wherein said group is optionally substituted with hydroxy or one or two of methyl;

$R^4$, $R^5$, $R^6$ and $R^7$ independently are hydrogen, Cl, Br or F; and
Q is $$\underset{N}{\overset{O-N}{\bigtriangleup}}R^1 \text{ or } \underset{N}{\overset{N-O}{\bigtriangleup}}R^1$$

wherein $R^1$ is cyclopropyl; or
a pharmaceutically acceptable salt or hydrate thereof.

27. A pharmaceutical composition comprising a compound according to claim 25 together with a pharmaceutically-acceptable carrier or diluent.

28. The pharmaceutical composition according to claim 27 in the form of an oral dosage unit containing 1–100 mg of the active compound.

29. A method for treating a central nervous system ailment associated with benzodiazepine receptors, comprising administering to a subject in need thereof an effective amount of a compound according to claim 25.

30. A method for treating a central nervous system ailment associated with benzodiazepine receptors, comprising administering to a subject in need thereof a pharmaceutical composition according to claim 27.

31. A compound of formula I

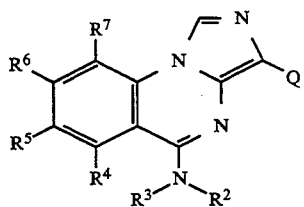

(I)

wherein
R² is hydrogen, C₁₋₆-alkyl, C₁₋₆-alkyl substituted with hydroxy, C₁₋₆-alkoxy, —C₁₋₆-alkyl-C₁₋₆-alkoxy, —C₁₋₆-alkyl-carbonyl-C₁₋₆-alkoxy, dimethoxyethyl, C₁₋₆-alkylsubstituted with formyl, C₁₋₆-alkyl substituted with 1,3-dioxolan-2-yl and R³ is C₁₋₆-alkyl substituted with C₃₋₇-cycloalkyl, C₁₋₆-alkyl substituted with di-C₁₋₆-alkylamino, phenyl, or a piperidinyl group optionally substituted with C₁₋₆-alkyl; or R² is C₁₋₆-alkyl substituted with C₃₋₇-cycloalkyl, C₁₋₆-alkyl substituted with di-C₁₋₆-alkylamino, phenyl, or a piperidinyl group optionally substituted with C₁₋₆-alkyl and R³ is hydrogen, C₁₋₆-alkyl, C₁₋₆-alkyl substituted with hydroxy, C₁₋₆-alkoxy, —C₁₋₆-alkyl-C₁₋₆-alkoxy, —C₁₋₆-alkyl-carbonyl-C₁₋₆-alkoxy, dimethoxyethyl, C₁₋₆-alkyl substituted with formyl, C₁₋₆-alkyl substituted with dioxolanyl; or R² and R³ independently are C₁₋₆-alkyl substituted with C₃₋₇-cycloalkyl, C₁₋₆-alkyl substituted with di-C₁₋₆-alkylamino, phenyl, or a piperidinyl group optionally substituted with C₁₋₆-alkyl;

R⁴, R⁵, R⁶ and R⁷ independently are hydrogen, hydroxy, Cl, Br, F, I, trifluoromethyl, nitro, amino, cyano, straight or branched C₁₋₆-alkyl, C₂₋₆-alkenyl, C₂₋₆-alkynyl, C₁₋₆-alkoxy, —C₁₋₆-alkyl-C₁₋₆-alkoxy or -carbonyl-C₁₋₆-alkoxy; and Q is

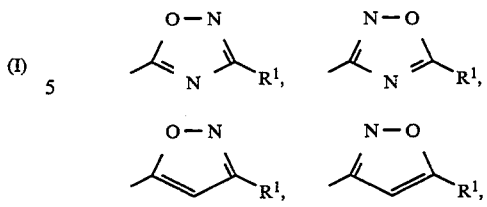

—COOR⁸ or —CN, wherein R¹ is hydrogen, straight or branched C₁₋₆-alkyl, C₃₋₇-cycloalkyl, C₁₋₆-alkoxy, —C₁₋₆-alkyl-C₁₋₆-alkoxy or trifluoromethyl; and R⁸ is straight or branched C₁₋₆-alkyl; or a pharmaceutically acceptable salt or hydrate thereof.

32. A compound according to claim 31, wherein
R² is hydrogen, methyl or ethyl and R³ is methyl substituted with cyclopropyl, ethyl substituted with dimethylamino, or a piperidinyl group optionally substituted with methyl; or R² is methyl substituted with cyclopropyl, ethyl substituted dimethylamino or a piperidinyl group optionally substituted with methyl and R³ is hydrogen, methyl or ethyl;
R⁴, R⁵, R⁶ and R⁷ independently are hydrogen, Cl, Br or F; and
Q is

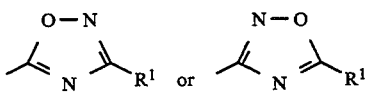

wherein R¹ is cyclopropyl; or
a pharmaceutically acceptable salt or hydrate thereof.

33. A pharmaceutical composition comprising a compound according to claim 31 together with a pharmaceutically-acceptable carrier or diluent.

34. The pharmaceutical composition according to claim 33 in the form of an oral dosage unit containing 1–100 mg of the active compound.

35. A method for treating a central nervous system ailment associated with benzodiazepine receptors, comprising administering to a subject in need thereof an effective amount of a compound according to claim 31.

36. A method for treating a central nervous system ailment associated with benzodiazepine receptors, comprising administering to a subject in need thereof a pharmaceutical composition according to claim 33.

* * * * *